United States Patent
Osawa et al.

(10) Patent No.: US 9,732,125 B2
(45) Date of Patent: Aug. 15, 2017

(54) POLYPEPTIDE PARTICLE AND METHOD FOR PRODUCING SAME

(71) Applicant: SPIBER INC., Tsuruoka-shi, Yamagata (JP)

(72) Inventors: Toshiaki Osawa, Tsuruoka (JP); Keisuke Morita, Tsuruoka (JP)

(73) Assignee: SPIBER INC., Yamagata (JP)

( * ) Notice: Subject to any disclaimer, the term of this patent is extended or adjusted under 35 U.S.C. 154(b) by 0 days.

(21) Appl. No.: 14/764,472

(22) PCT Filed: Apr. 18, 2014

(86) PCT No.: PCT/JP2014/061043
§ 371 (c)(1),
(2) Date: Jul. 29, 2015

(87) PCT Pub. No.: WO2014/175179
PCT Pub. Date: Oct. 30, 2014

(65) Prior Publication Data
US 2015/0376247 A1    Dec. 31, 2015

(30) Foreign Application Priority Data

Apr. 25, 2013 (JP) .................................. 2013-092848

(51) Int. Cl.

| | |
|---|---|
| C07K 14/435 | (2006.01) |
| A61K 8/64 | (2006.01) |
| A61K 8/42 | (2006.01) |
| A61K 8/46 | (2006.01) |
| A61Q 19/00 | (2006.01) |
| A61K 8/02 | (2006.01) |
| C08J 3/12 | (2006.01) |
| C08L 89/00 | (2006.01) |
| C09D 7/12 | (2006.01) |
| C08J 3/05 | (2006.01) |
| C08J 3/07 | (2006.01) |
| A61K 47/42 | (2017.01) |
| A61K 9/51 | (2006.01) |

(52) U.S. Cl.
CPC ...... *C07K 14/43518* (2013.01); *A61K 8/0279* (2013.01); *A61K 8/42* (2013.01); *A61K 8/46* (2013.01); *A61K 8/64* (2013.01); *A61Q 19/00* (2013.01); *C08J 3/05* (2013.01); *C08J 3/07* (2013.01); *C08J 3/12* (2013.01); *C08L 89/00* (2013.01); *C09D 7/125* (2013.01); *C09D 7/1275* (2013.01); *A61K 9/5169* (2013.01); *A61K 47/42* (2013.01); *A61K 2800/412* (2013.01); *A61K 2800/56* (2013.01); *A61K 2800/84* (2013.01); *C08J 2389/00* (2013.01)

(58) Field of Classification Search
None
See application file for complete search history.

(56) References Cited

U.S. PATENT DOCUMENTS

| 5,853,764 A | 12/1998 | Tsubouchi |
|---|---|---|
| 8,153,591 B2 * | 4/2012 | Masters .................. A61K 8/64 |
| | | 514/17.2 |
| 2007/0187862 A1 | 8/2007 | Kaplan et al. |
| 2007/0214520 A1 | 9/2007 | Scheibel et al. |
| 2008/0141792 A1 | 6/2008 | Li et al. |
| 2009/0123967 A1 | 5/2009 | Scheibel |
| 2010/0278883 A1 | 11/2010 | Liebmann et al. |
| 2011/0136669 A1 | 6/2011 | Liebmann et al. |
| 2012/0148639 A1 | 6/2012 | Tamada et al. |
| 2013/0109762 A1 | 5/2013 | Lammel et al. |
| 2014/0086874 A1 * | 3/2014 | Nazhat ............. C07K 14/43586 |
| | | 424/93.1 |
| 2014/0245923 A1 | 9/2014 | Sugahara et al. |

(Continued)

FOREIGN PATENT DOCUMENTS

| CN | 1560136 | 1/2005 |
|---|---|---|
| CN | 102176904 | 9/2011 |
| CN | 102344686 | 2/2012 |

(Continued)

OTHER PUBLICATIONS

Schacht et al.: "Controlled Hydrogel Formation of a Recombinant Spider Silk Protein"; Biomacromolecules, (2011), 12(7), pp. 2488-2495.
Japanese Office Action, Jul. 23, 2015; Japanese Patent Application No. 2015-513727 with English translation (10 pages).
Rammensee et al.: "Rheological characterization of hydrogels formed by recombinantly produced spider silk"; Appl. Phys. A Matr Sci. Process, 2006, vol. 82, No. 2, pp. 261-264.
Vepari C. et al.: "Silk as a biomaterial"; Polym. Sci., 2007, vol. 32, No. 8-9, pp. 991-1007.
Co-pending U.S. Appl. No. 14/764,455.
Co-pending U.S. Appl. No. 14/764,463.
Hofer et al.: "Recombinant spider silk particles for controlled delivery of protein drugs"; Biomaterials, (2012), vol. 33, pp. 1554-1562.

(Continued)

*Primary Examiner* — Anand Desai
(74) *Attorney, Agent, or Firm* — Hamre, Schumann, Mueller & Larson, P.C.

(57) ABSTRACT

Polypeptide particles of the present invention are particles of a polypeptide derived from spider silk proteins, and have an average particle size of 1000 nm or less. A method for producing polypeptide particles of the present invention includes: a solution production step in which the polypeptide is dissolved in at least one solvent selected from the group consisting of DMSO, DMF, and these with an inorganic salt, so as to obtain a solution of the polypeptide; a step in which the solution produced in the solution production step is substituted with a water-soluble solvent so as to obtain an aqueous solution of the polypeptide; and a step in which the aqueous solution of the polypeptide is dried. Thereby, the present invention provides polypeptide particles suitable for application to a living body and capable of being applied to cosmetics, etc., while identifying the properties of the polypeptide particles, and a method for producing the same.

7 Claims, 2 Drawing Sheets

(56) References Cited

U.S. PATENT DOCUMENTS

2015/0344542 A1   12/2015   Osawa et al.

FOREIGN PATENT DOCUMENTS

| | | |
|---|---|---|
| EP | 2 990 413 | 3/2016 |
| JP | 1-118544 | 5/1989 |
| JP | 2-240165 | 9/1990 |
| JP | 11-217506 | 8/1999 |
| JP | 2002-186847 | 7/2002 |
| JP | 2006-249115 | 9/2006 |
| JP | 2007-515391 | 6/2007 |
| JP | 2008-506409 | 3/2008 |
| JP | 2009-505668 | 2/2009 |
| JP | 2012-082241 | 4/2012 |
| JP | 2012-082244 | 4/2012 |
| JP | 2 774 934 | 9/2014 |
| JP | 2 940 033 | 11/2015 |
| RU | 2478706 | 4/2013 |
| WO | 2004/062697 | 7/2004 |
| WO | 2005/124011 | 12/2005 |
| WO | 2007/082936 | 7/2007 |
| WO | 2007/100524 | 9/2007 |
| WO | 2010/015419 | 2/2010 |
| WO | 2011/021712 | 2/2011 |
| WO | 2011/063990 | 6/2011 |
| WO | 2012/074588 | 6/2012 |

OTHER PUBLICATIONS

International Search Report, Jul. 15, 2014; PCT/JP2014/061043.
Extended European Search issued for corresponding European Patent Application No. 14788691.5, Dec. 6, 2016, 8 pages.
Rabotyagova, et al., "Self-Assembly of Genetically Engineered Spider Silk Block Copolymers", Biomacromolecules, vol. 10, No. 2, Jan. 2009, pp. 229-326.
Fu, et al., "Animal silks: their structures, properties and artificial production", Chemical Communications, No. 43, Jan. 2009, pp. 6515-6529.
Um, et al., "Wet spinning of silk polymer I. Effect of coagulation conditions on the morphological feature of filament", International Journal of Biological Macromolecules, vol. 34, No. 1-2, Apr. 2004, pp. 89-105.
Extended European Search Report issued in corresponding European Patent Application No. 14787823.5, Oct. 10, 2016, 12 pages.
Extended European Search Report issued in corresponding European Patent Application No. 14787816.9, Sep. 7, 2016, 8 pages.
Office Action issued in corresponding Chinese Patent Application No. 201480005729.6, Nov. 14, 2016, 14 pages with a machine translation.
Diao, et al., "Solubility and Electrospun Regenerated Fiber of Two Different Kinds of Spider Silk", Journal of Materials Science & Engineering, vol. 26, No. 6, Dec. 2008. pp. 918-922—English Abstract.

\* cited by examiner

… … …

POLYPEPTIDE PARTICLE AND METHOD FOR PRODUCING SAME

TECHNICAL FIELD

The present invention relates to polypeptide particles derived from spider silk proteins, and a method for producing the same.

BACKGROUND ART

Polypeptides have been studied for application to biomaterials, etc. Patent Document 1 proposes a hydrogel, a film, a sponge-like foam, etc., obtained by dissolving silk fibroin in a hygroscopic polymer such as polyethylene glycol. Patent Document 2 discloses a photocrosslinked aggregate made from spider silk.

PRIOR ART DOCUMENTS

Patent Documents

Patent Document 1: JP 2007-515391 A
Patent Document 2: JP 2008-506409 A

DISCLOSURE OF INVENTION

Problem to be Solved by the Invention

However, an urea aqueous solution, which is a conventionally proposed solvent, does not have a sufficient power to dissolve spider silk proteins, and a guanidine aqueous solution, hexafluoroisopropanol (HFIP), and the like are expensive and have a problem in application to a human body when they remain in a product. Further, the properties of silk fibroin particles have not been identified at all.

To solve the above conventional problems, the present invention provides polypeptide particles suitable for application to a living body, and a method for producing the same. Another problem to be solved by the present invention is to identify the properties of polypeptide particles derived from spider silk proteins.

Means for Solving Problem

Polypeptide particles of the present invention are particles of a polypeptide derived from spider silk proteins, wherein the polypeptide includes a water-soluble polypeptide, and the polypeptide particles have an average particle size of 1000 nm or less. Incidentally, the water-soluble polypeptide used herein includes a polypeptide that is dissolved completely in a water-soluble solvent or a polypeptide that is dispersed in a water-soluble solvent and thus substantially is in a dissolved state.

A method for producing polypeptide particles of the present invention includes: a solution production step in which a polypeptide derived from spider silk proteins is dissolved in at least one dissolving solvent selected from the group consisting of: (A) dimethyl sulfoxide; (B) dimethyl sulfoxide with an inorganic salt; and (C) N, N-dimethylformamide with an inorganic salt, so as to obtain a solution of the polypeptide; a step in which the solution of the polypeptide produced in the solution production step is substituted with a water-soluble solvent so as to obtain an aqueous solution of the polypeptide; and a step in which the aqueous solution of the polypeptide is dried. Incidentally, "aqueous solution of the polypeptide" used herein includes both of an aqueous solution in which a polypeptide is completely dissolved, and an aqueous solution in which polypeptide microparticles are dispersed and thus substantially take the form of an aqueous solution. Hereinafter, the expression shall have the same meaning as described above. Further, "a polypeptide is dissolved in a dissolving solvent" used herein includes both of a state in which a polypeptide is completely dissolved in a dissolving solvent and a state in which polypeptide microparticles are dispersed in a dissolving solvent and thus are substantially dissolved in the dissolving solvent. Hereinafter, the expression shall have the same meaning as described above.

Effect of the Invention

In the present invention, by using a specific solvent in the production of the polypeptide solution, substituting the solution with a water-soluble solvent to obtain an aqueous solution of the polypeptide, and drying the obtained aqueous solution, polypeptide particles in which the amount of the remaining solvent is little or the amount of the remaining solution is sufficiently low can be provided. Further, since the average particle size of the polypeptide particles of the present invention is sufficiently small, more particles can adhere to a predetermined substrate surface such as a medicament and perfume, as compared with particles having a larger average particle size. Therefore, when the polypeptide particles of the present invention are attached to the substrate surface such as a medicament and perfume, they can effectively delay an exposure of the substrate surface even if their individual decomposition rate on the substrate surface and the desorption speed from the substrate surface are the same as those of particles having a larger average particle size. As a result, the polypeptide particles of the present invention can exhibit an excellent property of slowly releasing an effect of the medicament or perfume advantageously.

Incidentally, in the particles of the present invention, those substantially spherical in shape are used favorably as components of cosmetics, paints, etc. Additionally, the solvents used in the present technique are those that have been used in the production of acrylic fibers and polyimid resin, and they are low cost.

DESCRIPTION OF THE INVENTION

Figure 1:
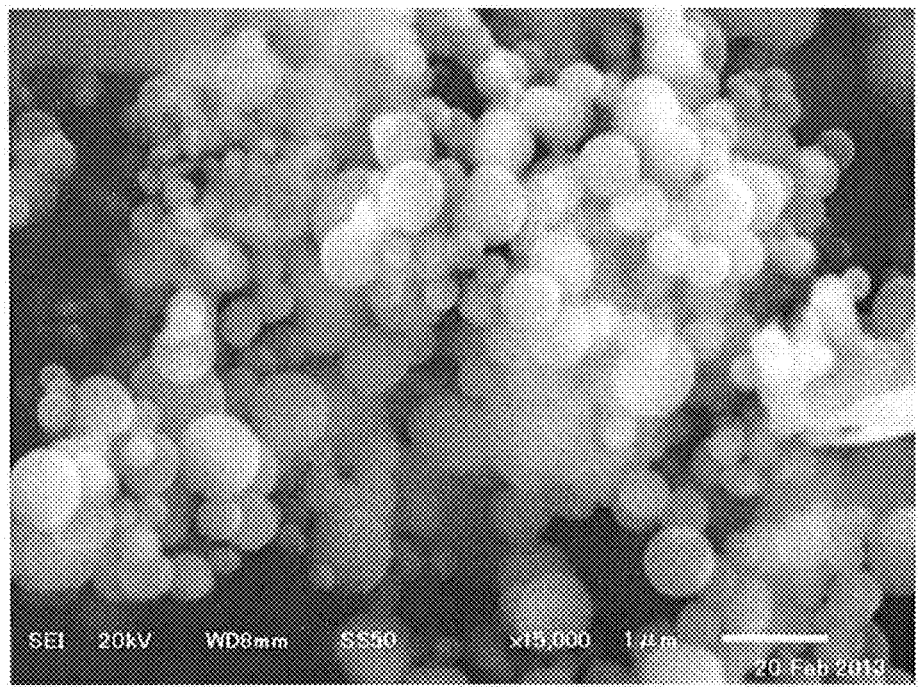
FIG. 1 is a photograph of polypeptide particles of Example 1 of the present invention taken by a scanning electron microscope (SEM) (15,000× magnification).

A polypeptide derived from spider silk proteins is used as the protein of the present invention. The polypeptide derived from spider silk proteins is not limited particularly as long as it is derived from or similar to natural type spider silk proteins. Examples of the polypeptide derived from spider silk proteins include variants, analogs, derivatives, and the like of natural type spider silk proteins. In terms of excellent tenacity, the recombinant spider silk protein preferably is a recombinant spider silk protein derived from major dragline silk proteins produced in major ampullate glands of spiders.

Examples of the major dragline silk proteins include major ampullate spidroins MaSp1 and MaSp2 derived from *Nephila clavipes*, and ADF3 and ADF4 derived from *Araneus diadematus*, etc.

The recombinant spider silk protein may be a recombinant spider silk protein derived from minor dragline silk produced in minor ampullate glands of spiders. Examples of the minor dragline silk proteins include minor ampullate spidroins MiSp1 and MiSp2 derived from *Nephila clavipes*.

Other than these, the recombinant spider silk protein may be a recombinant spider silk protein derived from flagelliform silk proteins produced in flagelliform glands of spiders. Examples of the flagelliform silk proteins include flagelliform silk proteins derived from *Nephila clavipes*, etc.

Examples of the polypeptide derived from major dragline silk proteins include a polypeptide containing two or more units of an amino acid sequence represented by the formula 1: REP1-REP2 (1), preferably a polypeptide containing four or more units thereof, and more preferably a polypeptide containing six or more units thereof. In the polypeptide derived from major dragline silk proteins, units of the amino acid sequence represented by the formula (1): REP1-REP2 (1) may be the same or different from each other. In the formula (1), the REP1 represents polyalanine. In the REP1, the number of alanine residues arranged in succession is preferably 2 or more, more preferably 3 or more, further preferably 4 or more, and particularly preferably 5 or more. Further, in the REP1, the number of alanine residues arranged in succession is preferably 20 or less, more preferably 16 or less, further preferably 14 or less, and particularly preferably 12 or less. In the formula (1), the REP2 is an amino acid sequence composed of 10 to 200 amino acid residues. The total number of glycine, serine, glutamine, proline, and alanine residues contained in the amino acid sequence is 40% or more, preferably 50% or more, and more preferably 60% or more with respect to the total number of amino acid residues contained therein.

In the major dragline silk, the REP1 corresponds to a crystal region in a fiber where a crystal β sheet is formed, and the REP2 corresponds to an amorphous region in a fiber where most of the parts lack regular structures and that has more flexibility. Further, the [REP1-REP2] corresponds to a repetitious region (repetitive sequence) composed of the crystal region and the amorphous region, which is a characteristic sequence of dragline silk proteins.

An example of the polypeptide containing two or more units of the amino acid sequence represented by the formula 1: REP1-REP2 (1) is a recombinant spider silk protein derived from ADF3 having an amino acid sequence represented by any of SEQ ID NO: 1, SEQ ID NO: 2, SEQ ID NO: 3, and SEQ ID NO: 4. The amino acid sequence represented by SEQ ID NO: 1 is an amino acid sequence from the 1st residue to the 542nd residue of an amino acid sequence that is obtained by adding an amino acid sequence (SEQ ID NO: 5) composed of a start codon, an His 10-tag and an HRV3C Protease (Human rhinovirus 3C Protease) recognition site to the N-terminal of a partial amino acid sequence of ADF3 obtained from the NCBI database (NCBI Genebank Accession No.: AAC47010, GI: 1263287). The amino acid sequence represented by SEQ ID NO: 2 is an amino acid sequence obtained by the following mutation: in an amino acid sequence of ADF3 to the N-terminal of which has been added the amino acid sequence (SEQ ID NO: 5) composed of a start codon, an His 10-tag and an HRV3C Protease (Human rhinovirus 3C Protease) recognition site, 1st to 13th repetitive regions are about doubled and the translation ends at the 1154th amino acid residue. The amino acid sequence represented by SEQ ID NO: 3 is an amino acid sequence obtained by adding the amino acid sequence (SEQ ID NO: 5) composed of a start codon, an His 10-tag and an HRV3C Protease (Human rhinovirus 3C Protease) recognition site, to the N-terminal of a partial amino acid sequence of ADF3 (NCBI Genebank Accession No.: AAC47010, GI: 1263287) obtained from the NCBI database. The amino acid sequence represented by SEQ ID NO: 4 is an amino acid sequence obtained as follows: in an amino acid sequence of ADF3 (NCBI Genebank Accession No.: AAC47010, GI: 1263287) to the N-terminal of which has been added the amino acid sequence (SEQ ID NO: 5) composed of a start codon, an His 10-tag and an HRV3C Protease (Human rhinovirus 3C Protease) recognition site, 1st to 13th repetitive regions are about doubled. Further, the polypeptide containing two or more units of the amino acid sequence represented by the formula 1: REP1-REP2 (1) may be a polypeptide that is composed of an amino acid sequence represented by any of SEQ ID NO: 1, SEQ ID NO: 2, SEQ ID NO: 3 and SEQ ID NO: 4 in which one or a plurality of amino acids have been substituted, deleted, inserted and/or added and that has repetitious regions composed of crystal regions and amorphous regions.

In the present invention, "one or a plurality of" refers to 1 to 40, 1 to 35, 1 to 30, 1 to 25, 1 to 20, 1 to 15, 1 to 10, or 1 or a few, for example. Further, in the present invention, "one or a few" refers to 1 to 9, 1 to 8, 1 to 7, 1 to 6, 1 to 5, 1 to 4, 1 to 3, 1 to 2, or 1.

An example of the recombinant spider silk protein derived from minor dragline silk proteins is a polypeptide containing an amino acid sequence represented by the formula 2: REP3 (2). In the formula 2, the REP 3 indicates an amino acid sequence composed of (Gly-Gly-Z)$_m$(Gly-Ala)$_l$(A)$_r$, where Z indicates any one of amino acids, in particular, it preferably is an amino acid selected from the group consisting of Ala, Tyr and Gln. Further, preferably, m is 1 to 4, l is 0 to 4, and r is 1 to 6.

Among spider silks, the minor dragline silk is wound spirally from the center of a spider net, and used as a reinforcement of the net and a yarn to wrap a captured prey. The minor dragline silk is inferior to the major dragline silk in tensile strength, but is known to have high stretchability. The reason for this is considered to be as follows: in the minor dragline silk, since many crystal regions are formed of regions where glycine and alanine are arranged alternately in succession, hydrogen bonds in the crystal regions weaken easily as compared with the major dragline silk whose crystal regions are formed only of alanine.

Examples of the recombinant spider silk protein derived from flagelliform silk proteins include a polypeptide containing an amino acid sequence represented by the formula 3: REP4 (3). In the formula 3, the REP 4 indicates an amino acid sequence composed of (Gly-Pro-Gly-Gly-X)$_n$, where X indicates any one of amino acids, in particular, it preferably is an amino acid selected from the group consisting of Ala, Ser, Tyr and Val. Further, n indicates a number of 4 or larger, preferably 10 or larger, and more preferably 20 or larger.

Among spider silks, the flagelliform silk does not have crystal regions but has repetitious regions composed of amorphous regions, which is a major characteristic of the flagelliform silk. It is considered that since the major dragline silk and the like have repetitious regions composed of crystal regions and amorphous regions, they have both of high strength and stretchability. Meanwhile, regarding the flagelliform silk, the strength is inferior to that of the major dragline silk but the stretchability is high. The reason for this is considered to be that the flagelliform silk is composed mostly of amorphous regions.

The polypeptide can be produced using a host that has been transformed by an expression vector containing a gene encoding a polypeptide. A method for producing a gene is not limited particularly, and it may be produced by amplifying a gene encoding a natural type spider silk protein from a cell containing the desired gene of spider by a polymerase chain reaction (PCR), etc., and cloning it, or may be synthesized chemically. A method for chemically synthesizing a gene also is not limited particularly, and it can be synthesized as follows, for example: based on information of amino acid sequences of natural type spider silk proteins obtained from the NCBI web database, oligonucleotides that have been synthesized automatically with AKTA oligopilot plus 10/100 (GE Healthcare Japan Corporation) are linked by PCR, etc. At this time, in order to facilitate purification and observation of protein, a gene may be synthesized that encodes a protein composed of an amino acid sequence in which an amino acid sequence composed of a start codon and an His 10-tag has been added to the N-terminal of the amino acid sequence. Examples of the expression vector include a plasmid, a phage, a virus, and the like that can express protein based on a DNA sequence. The plasmid-type expression vector is not limited particularly as long as it allows a target gene to be expressed in a host cell and it can amplify itself. For example, in the case of using *Escherichia coli* Rosetta (DE3) as a host, a pET22b(+) plasmid vector, a pCold plasmid vector, and the like can be used. Among these, in terms of productivity of protein, the use of the pET22b(+) plasmid vector is preferred. Examples of the host include animal cells, plant cells, microbes, etc.

Further, examples of the polypeptide include a water-soluble polypeptide that is dissolved completely in a water-soluble solvent or a polypeptide that is dispersed in a water-soluble solvent and thus is substantially in a dissolved state when the solution produced in the solution production step is substituted with the water-soluble solvent. Incidentally, regardless of the properties of the polypeptide, for example, by lowering the concentration of the polypeptide in the solution produced in the solution production step, substantially an aqueous solution of the polypeptide in which the polypeptide is dispersed can be obtained when the solution is substituted with the water-soluble solvent. Further, such dispersion of peptide may be caused by increasing the temperature from a low-temperature state to a high-temperature state. In other words, the polypeptide particles include, as the polypeptide, a polypeptide that can be dissolved in a water-soluble solvent or, for example, nano-sized polypeptide microparticles that can be dispersed in a water-soluble solvent and thus substantially form an aqueous solution when the solution produced in the solution production step is substituted with the water-soluble solvent.

The average particle size of the polypeptide particles of the present invention is 1000 nm or less. The preferable lower limit is 246 nm. Within the above range, the polypeptide particles can have favorable sliding properties, filtration can be performed, and they will be advantageous in cost. When the average particle size exceeds 1000 nm, the specific surface area of the polypeptide particles tends to decrease. When the average particle size is less than 246 nm, filtration tends to be difficult. Preferably, the shape of the polypeptide particles is spherical. The spherical polypeptide particles can be close-packed while having good sliding properties. Therefore, the spherical polypeptide particles are suitable as components of cosmetics or paints.

The polypeptide particles of the present invention are produced by: a solution production step in which a polypeptide derived from spider silk proteins is dissolved in at least one dissolving solvent selected from the group consisting of: (A) dimethyl sulfoxide; (B) dimethyl sulfoxide with an inorganic salt; and (C) N, N-dimethylformamide with an inorganic salt, so as to obtain a solution of the polypeptide; a step in which the solution of the polypeptide produced in the solution production step is substituted with a water-soluble solvent so as to obtain an aqueous solution of the polypeptide; and a step in which the aqueous solution of the polypeptide is dried. Further, at least one selected from the group consisting of dimethyl sulfoxide and N, N-dimethylformamide may be present inside the obtained polypeptide particles. The amount of the dissolving solvent present therein is not limited particularly, and it is an amount that remains therein unintentionally after the solution produced in the solution production step is substituted with the water-soluble solvent.

In addition to the substances indicated in (A)-(C) above, the dissolving solvent may contain alcohol and/or water. The dissolving solvent is a polar solvent, and tends to absorb moisture in air. Therefore, in some cases, commercial solvents contain several % of water. The dissolving solvent may contain this amount of water and/or alcohol. Incidentally, the substances functioning as the dissolving solvent are those indicated in (A)-(C) above.

The water-soluble solvent refers to a solvent containing water. Examples of the water-soluble solvent include water, a water-soluble buffer solution, and saline. In terms of high compatibility with the human body, preferably, the water-soluble solvent is water. Although the water is not limited particularly, it may be pure water, distilled water, ultrapure water, etc.

In the present invention, a solvent containing DMSO and/or DMF (polar solvent) is used as the solvent. DMSO has a melting point of 18.4° C. and a boiling point of 189° C. DMF has a melting point of −61° C. and a boiling point of 153° C. DMSO and DMF have much higher boiling points than hexafluoroisopropanol (HFIP) and hexafluoroacetone (HFAc) having boiling points of 59° C. and −26.5° C., respectively, which have been used in conventional methods, and hence DMSO and DMF have favorable dissolubility. Further, in view of the fact that DMSO and DMF have been used also in general industrial fields for acrylic fiber polymerization, acrylic fiber spinning solutions, and solvents for polyimide polymerization, they are low-cost substances with proven safety.

Addition of an inorganic salt to DMSO or DMF further increases the solubility of a solute. The inorganic salt is at least one selected from alkali metal halides (e.g., LiCl, LiBr, etc), alkaline-earth metal halides (e.g., $CaCl_2$), alkaline-earth metal nitrate (e.g., $Ca(NO_3)_2$, etc.), and sodium thiocyanate (e.g., NaSCN, etc.). When the dissolved components are assumed to be 100 mass %, the percentage of the inorganic salt preferably ranges from 0.1 to 20 mass %.

The aqueous solution of the polypeptide is produced by substituting the solvent with the water-soluble solvent. Further, preferably, the step of substituting the solvent with the water-soluble solvent is performed in the following manner: the solution of the polypeptide obtained by dissolving the polypeptide in the solvent is placed in a dialysis membrane, the dialysis membrane is immersed in a water-soluble solvent, and the water-soluble solvent is renewed at least one time. Specifically, preferably, the step of substituting the solvent with the water-soluble solvent is performed by placing the solution after the solution production step in a dialysis membrane, leaving it to stand for 3 hours in a water-soluble solvent in an amount 100 times or more the amount of the solution (one batch), and renewing the water-soluble solvent three or more times. Any dialysis membrane that does not allow the polypeptide in the solution to pass therethrough can be used. An example of the dialysis membrane is a cellulose dialysis membrane. By repeating the substitution using the water-soluble solvent, the amount of the dissolving solvent can be reduced close to zero. In the latter half of the desolvation step, it is unnecessary to use a dialysis membrane.

The amount of the solvent, i.e., dimethyl sulfoxide (DMSO) or N, N-dimethylformamide (DMF), remaining in the polypeptide after the substitution step using the water-soluble solvent can be measured by a nuclear magnetic resonance spectrometer (NMR). A 1,2-dichloroethane-formic acid solution can be used as an internal standard.

In the drying step, preferably, vacuum freeze-drying is adopted. The degree of vacuum at vacuum freeze-drying is preferably 200 Pa or less, more preferably 150 Pa or less, and further preferably 100 Pa or less. By vacuum drying, water evaporates from the aqueous solution of the polypeptide, and the temperature declines by the evaporation latent heat, whereby it is brought into a frozen state. The temperature of the polypeptide at vacuum freeze-drying is preferably 70° C. or less, more preferably 60° C. or less, and further preferably 50° C. or less. Incidentally, prior to vacuum freeze-drying, the aqueous solution of the polypeptide may be pre-frozen at a temperature of −10° C. to −45° C. for about 10 to 36 hours. The moisture content after freeze-drying is preferably 5.0% or less, and more preferably 3.0% or less.

EXAMPLES

Hereinafter, the present invention will be described in further detail by way of examples. Note that the present invention is not limited to the following examples. Water is used as the water-soluble solvent in the examples.

<Methods of Various Measurements>

(1) Measurement of Remaining Amount of Solvent

As an internal standard, a 1,2-dichloroethane-formic acid solution at a concentration of 3,100 ppm (0.00310 mg/ml) was prepared. 500 µl of a protein solution (obtained by dissolving 0.1 g of polypeptide particles in 10 ml of formic acid) and 500 µl of an internal standard solution were mixed. For H-NMR measurement, an acetonitrile deuterated solvent was added to the mixed solution in an amount approximately equivalent to that of the mixture solution so as to dilute the solution to about two times. Then, H-NMR measurement was performed (NMR model: JNM-ECX 100 manufactured by JOEL Ltd.). The H-NMR integrated intensity of 1,2-dichloroethane (internal standard sample) was compared with the H-NMR integrated intensity of DMSO. A calibration curve was formed by preparing a DMSO-formic acid solution at 3 ppm to 3000 ppm and following the above-mentioned protocol. By comparison with the calibration curve, the concentration of DMSO in the protein solution was calculated. A nuclear magnetic resonator (NMR) manufactured by JOEL Ltd. was used for the measurement of the concentration of DMSO.

(2) Viscosity

An EMS machine manufactured by Kyoto Electronics Manufacturing Co., Ltd. was used.

(3) Average Particle Size

An average value of 100 particles was calculated by observation of photographs taken by a scanning electron microscope (SEM) (15,000× magnification).

Example 1

1. Preparation of Polypeptide
<Gene Synthesis of ADF3Kai-NN>

A partial amino acid sequence of ADF3, which is one of two principal dragline silk proteins of *Araneus diadematus*, was obtained from the NCBI web database (NCBI Accession No.: AAC47010, GI: 1263287), and an amino acid sequence (SEQ ID NO: 5) composed of a start codon, an His 10-tag and an HRV3C Protease (Human rhinovirus 3C Protease) recognition site was added to the N-terminal of the partial amino acid sequence of ADF3, so as to synthesize a gene encoding a polypeptide (ADF3Kai-NN) composed of an amino acid sequence (SEQ ID NO: 1), i.e., the 1st residue to the 542nd residue from the N-terminal of the resultant sequence. Consequently, a pUC57 vector to which a gene of ADF3Kai-NN composed of a base sequence represented by SEQ ID NO: 6 had been introduced was obtained (having an Nde I site immediately upstream of the 5' terminal of the gene and an Xba I site immediately downstream of the 5' terminal thereof). Thereafter, the gene was subjected to a restriction enzyme treatment with Nde I and EcoR I, and recombined into a pET22b(+) expression vector. Thus, a pET22b(+) vector to which the gene of ADF3Kai-NN had been introduced was obtained.

<Expression of Protein>

The obtained pET22b(+) expression vector containing the gene sequence of ADF3Kai-NN was transformed into *Escherichia coli* Rosetta (DE3). The obtained single colony was incubated for 15 hours in 2 mL of an LB culture medium containing ampicillin. Thereafter, 1.4 ml of said culture solution was added to 140 mL of an LB culture medium containing ampicillin, and incubated to an $OD_{600}$ of 3.5 under the conditions of 37° C. and 200 rpm. Next, the culture solution with the $OD_{600}$ of 3.5 was added to 7 L of a 2×YT culture medium containing ampicillin, together with 140 mL of 50% glucose, and incubated further to the $OD_{600}$ of 4.0. Thereafter, isopropyl-β-thiogalactopyranoside (IPTG) was added to the obtained culture solution with the $OD_{600}$ of 4.0 so that the final concentration would be 0.5 mM, thereby inducing the expression of protein. After a lapse of two hours from the addition of IPTG, the culture solution was centrifuged and bacterial cells were collected. Protein solutions prepared from the culture solution before the addition of IPTG and the culture solution after the addition of IPTG were each electrophoresed in a polyacrylamide gel. Consequently, a target band size (about 47.6 kDa) was observed with the addition of IPTG, and the expression of the target protein (ADF3Kai-NN) was confirmed.

Purification (1) About 50 g of bacteria cells of the *Escherichia coli* expressing the ADF3Kai-NN protein and 300 ml of a buffer solution AI (20 mM Tris-HCl, pH 7.4) were placed in a centrifuge tube (1000 ml). After dispersing the bacteria cells with a mixer ("T18 basic ULTRA TURRAX" manufactured by IKA, level 2), the dispersion was centrifuged (11,000 g, 10 minutes, room temperature) with a centrifuge ("Model 7000" manufactured by Kubota Corporation), and a supernatant was discarded.

(2) To a precipitate (bacteria cells) obtained by the centrifugation, 300 ml of the buffer solution AI and 3 ml of 0.1 M PMSF (dissolved by isopropanol) were added. After dispersing the precipitate for 3 minutes with the above mixer (level 2) manufactured by IKA, the bacteria cells were disrupted repeatedly for three times using a high-pressure homogenizer ("Panda Plus 2000" manufactured by GEA Niro Soavi).

(3) The disrupted bacterial cells were centrifuged (11,000 g×g, 30 minutes, room temperature) with the above centrifuge manufactured by Kubota Corporation.

(4) To a supernatant (soluble fraction protein) obtained by the centrifugation, Ni Sepharose (50% slurry, product number "17-5318-02" manufactured by GE Healthcare) was added, and the mixture was stirred for 60 minutes with a stirrer. Then, the resultant was centrifuged (500×g, five minutes, room temperature) with the above centrifuge manufactured by Kubota Corporation, and a supernatant was removed. The Ni Sepharose was filled in an empty column (product number "17-0435-01" manufactured by GE Healthcare) and washed with a buffer solution AI, and ADF3Kai-NN protein was eluted using an elution buffer (50 mM Tris, 50 mM NaCl, 300 mM imidazole, pH 7.5).

(5) The obtained eluate was desalted using an ultrafiltration membrane ("Amicon Ultra" manufactured by Merck Millipore Corporation). Thereafter, the obtained solution was freeze-dried to remove water, thereby collecting freeze-dried powder. The purification degree of the target protein ADF3Kai-NN (about 47.6 kDa) in the obtained freeze-dried powder was checked by analyzing images of the results of polyacrylamide gel electrophoresis (Oriole staining) of said protein powder using Imagelab (Bio-RAD Laboratories, Inc.). As a result, the purification degree of ADF3Kai-NN was about 69.1%.

2. Adjustment of Solution 0.5 g of spider silk protein powder (ADF3Kai-NN) was added to 10 ml of DMSO (containing 1M LiCl), followed by dissolution at 80° C. for 30 minutes. Then, the solution was placed a dialysis tube (Cellulose Tube 36/32 manufactured by Sanko Junyaku Co., Ltd. (presently EIDIA Co., Ltd)).

3. Substitution with Water

The dialysis tube was placed in a beaker filled with 3 L of pure water, left to stand for 3 hours, and water was renewed. This operation was repeated six times in total. Thereby, almost all of DMSO was substituted with water and an aqueous solution in which the polypeptide was dissolved or dispersed was obtained.

4. Vacuum Freeze-Drying

The aqueous solution of the polypeptide was freeze-dried by a freeze dryer ("FDU-1200" manufactured by Tokyo Rikakiki Co., Ltd.) under conditions of 14 Pa and −45° C. for 15 hours.

Results (1) Measurement of Remaining Amount of Solvent

The remaining amount of the solvent measured was 0.13 g based on 100 g of the polypeptide particles.

(2) Average Particle Size

The average particle size was 435 nm. The minimum value observed was 177 nm and the maximum value observed was 800 nm.

(3) FIG. 1 shows the obtained polypeptide particles.

Example 2

Polypeptide particles of Example 2 were tested in the same manner as in Example 1 except that a 10 mg/ml dope prepared by adding 30 ml of DMSO (without salt) to 0.3 g of protein was used. The following are the results.

(1) Average Particle Size

The average particle size was 478 nm. The minimum value observed was 200 nm and the maximum value observed was 911 nm.

Figure 2:
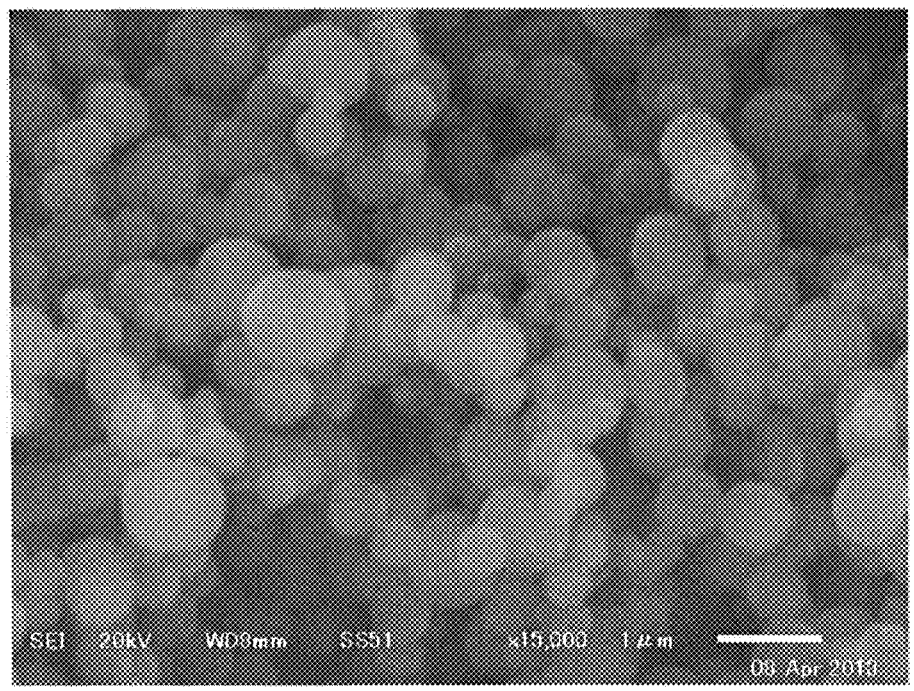
FIG. 2 is a photograph of polypeptide particles of Example 2 of the present invention taken by a scanning electron microscope (SEM) (15,000× magnification).

(2) FIG. 2 shows the obtained polypeptide particles.

Example 3

Polypeptide particles of Example 3 were tested in the same manner as in Example 1 except that a 10 mg/ml dope prepared by adding 30 ml of DMF and 1M LiCl to 0.3 g of protein was used. The following are the results.

(1) Average Particle Size

The average particle size was 246 nm. The minimum value observed was 133 nm and the maximum value observed was 422 nm.

Figure 3:
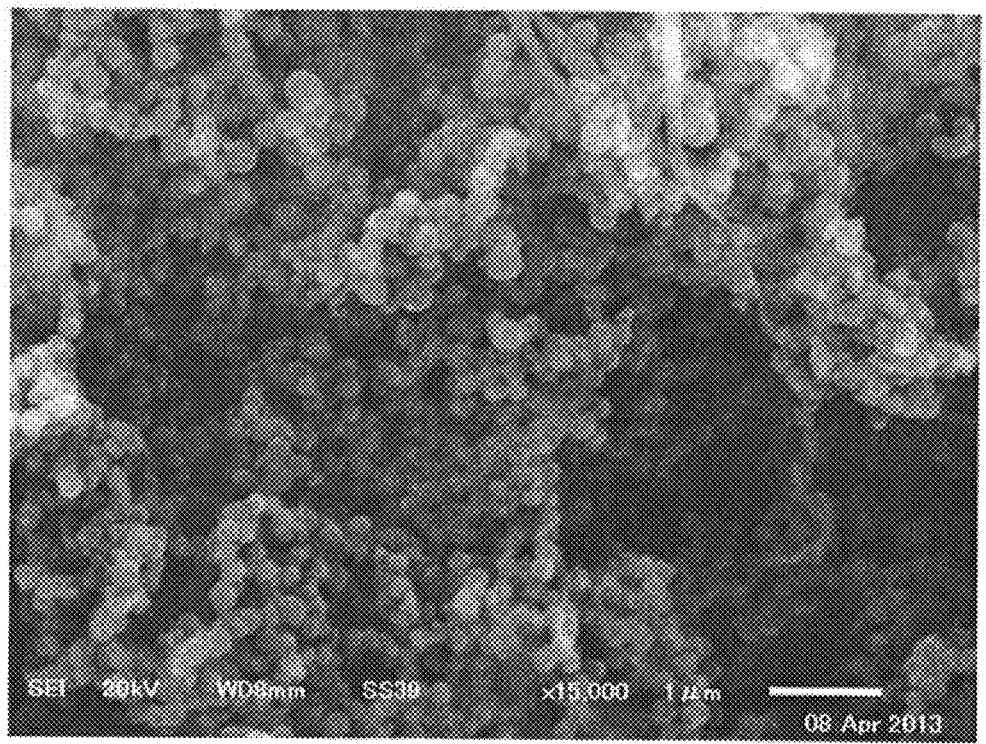
FIG. 3 is a photograph of polypeptide particles of Example 3 of the present invention taken by a scanning electron microscope (SEM) (15,000× magnification).

(2) FIG. 3 shows the obtained polypeptide particles.

Although water was used in the substitution step in the above Examples 1-3, the same effect can be obtained using other water-soluble solvents.

INDUSTRIAL APPLICABILITY

The polypeptide particles of the present invention are useful as components of cosmetics or paints, etc.

SEQUENCE LISTING FREE TEXT

SEQ ID NOS: 1-5 amino acid sequences
SEQ ID NO: 6 base sequence

The invention claimed is:

1. Polypeptide particles that are particles of a polypeptide derived from spider silk proteins,
the polypeptide particles having an average particle size of 1000 nm or less,
wherein at least one selected from the group consisting of dimethyl sulfoxide and N, N-dimethylformamide is present inside the polypeptide particles.

2. The polypeptide particles according to claim 1, wherein the polypeptide particles are spherical in shape.

3. A method for producing polypeptide particles, comprising:
a solution production step in which a polypeptide derived from spider silk proteins is dissolved in at least one dissolving solvent selected from the group consisting of: (A) dimethyl sulfoxide; (B) dimethyl sulfoxide with an inorganic salt; and (C) N, N-dimethylformamide with an inorganic salt, so as to obtain a solution of the polypeptide;
a step in which the solution of the polypeptide produced in the solution production step is substituted with a water-soluble solvent so as to obtain an aqueous solution of the polypeptide; and a step in which the aqueous solution of the polypeptide is dried.

4. The method for producing polypeptide particles according to claim 3, wherein the polypeptide particles are produced using an aqueous solution that is obtained by substituting the solution of the polypeptide with water.

5. The method for producing polypeptide particles according to claim 3, wherein the substitution step using the water-soluble solvent is a step in which the solution of the polypeptide obtained by dissolving the polypeptide in the dissolving solvent is placed in a dialysis membrane, the dialysis membrane is immersed in a water-soluble solvent, and the water-soluble solvent is renewed at least one time.

6. The method for producing polypeptide particles according to claim 3, wherein the drying is vacuum freeze-drying.

7. The polypeptide particles according to claim 1, wherein the polypeptide particles can be dissolved in a water-soluble solvent or can be dispersed in a water-soluble solvent.

\* \* \* \* \*

SEQUENCE LISTING

```
<160> NUMBER OF SEQ ID NOS: 6

<210> SEQ ID NO 1
<211> LENGTH: 542
<212> TYPE: PRT
<213> ORGANISM: Artificial
<220> FEATURE:
<223> OTHER INFORMATION: ADF3Kai-NN

<400> SEQUENCE: 1

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
```

```
                35                  40                  45
Pro Tyr Gly Pro Gly Ala Ser Ala Ala Ala Ala Ala Gly Gly Tyr
 50                  55                  60
Gly Pro Gly Ser Gly Gln Gln Gly Pro Ser Gln Gln Gly Pro Gly Gln
 65                  70                  75                  80
Gln Gly Pro Gly Gly Gln Gly Pro Tyr Gly Pro Gly Ala Ser Ala Ala
                 85                  90                  95
Ala Ala Ala Ala Gly Gly Tyr Gly Pro Gly Ser Gly Gln Gln Gly Pro
            100                 105                 110
Gly Gly Gln Gly Pro Tyr Gly Pro Gly Ser Ser Ala Ala Ala Ala Ala
            115                 120                 125
Ala Gly Gly Asn Gly Pro Gly Ser Gly Gln Gln Gly Ala Gly Gln Gln
            130                 135                 140
Gly Pro Gly Gln Gln Gly Pro Gly Ala Ser Ala Ala Ala Ala Ala Ala
145                 150                 155                 160
Gly Gly Tyr Gly Pro Gly Ser Gly Gln Gln Gly Pro Gly Gln Gln Gly
            165                 170                 175
Pro Gly Gly Gln Gly Pro Tyr Gly Pro Gly Ala Ser Ala Ala Ala Ala
            180                 185                 190
Ala Ala Gly Gly Tyr Gly Pro Gly Ser Gly Gln Gly Pro Gly Gln Gln
            195                 200                 205
Gly Pro Gly Gly Gln Gly Pro Tyr Gly Pro Gly Ala Ser Ala Ala Ala
            210                 215                 220
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gly Gln Gly Pro Tyr Gly
            245                 250                 255
Pro Gly Ala Ser Ala Ala Ala Ala Ala Ala Gly Gly Tyr Gly Pro Gly
            260                 265                 270
Tyr Gly Gln Gln Gly Pro Gly Gln Gln Gly Pro Gly Gln Gly Pro
            275                 280                 285
Tyr Gly Pro Gly Ala Ser Ala Ala Ser Ala Ala Ser Gly Gly Tyr Gly
            290                 295                 300
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Gly Gly
            325                 330                 335
Tyr Gly Pro Gly Ser Gly Gln Gln Gly Pro Gly Gln Gln Gly Pro Gly
            340                 345                 350
Gln Gln Gly Pro Gly Gln Gln Gly Pro Gly Gly Gln Gly Pro Tyr Gly
            355                 360                 365
Pro Gly Ala Ser Ala Ala Ala Ala Ala Gly Gly Tyr Gly Pro Gly
            370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
            405                 410                 415
Gln Gln Gly Pro Gly Gln Gln Gly Pro Gly Gln Gln Gly Pro Gly Gly
            420                 425                 430
Gln Gly Ala Tyr Gly Pro Gly Ala Ser Ala Ala Gly Ala Ala Gly
            435                 440                 445
Gly Tyr Gly Pro Gly Ser Gly Gln Gln Gly Pro Gly Gln Gln Gly Pro
            450                 455                 460
```

```
Gly Gln Gln Gly Pro Gly Gln Gly Pro Gly Gln Gly Pro Gly
465                 470                 475                 480

Gln Gln Gly Pro Gly Gln Gly Pro Gly Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gly Pro Gly Gln Gln Gly Pro
                515                 520                 525

Gly Gly Gln Gly Pro Tyr Gly Pro Gly Ala Ala Ser Ala Ala
            530                 535                 540

<210> SEQ ID NO 2
<211> LENGTH: 1154
<212> TYPE: PRT
<213> ORGANISM: Artificial
<220> FEATURE:
<223> OTHER INFORMATION: ADF3Kai-Large-NRSH1

<400> SEQUENCE: 2

Met His His His His His His His His Ser Ser Gly Ser Ser
1               5                   10                  15

Leu Glu Val Leu Phe Gln Gly Pro Ala Arg Ala Gly Ser Gln Gln
                20                  25                  30

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Gly Gly Tyr
50                  55                  60

Gly Pro Gly Ser Gly Gln Gln Gly Pro Ser Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
                100                 105                 110

Gly Gly Gln Gly Pro Tyr Gly Pro Gly Ser Ser Ala Ala Ala Ala
                115                 120                 125

Ala Gly Gly Asn Gly Pro Gly Ser Gly Gln Gln Gly Ala Gly Gln Gln
                130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gln Gly Pro Tyr Gly Pro Gly Ala Ser Ala Ala Ala Ala
                180                 185                 190

Ala Ala Gly Gly Tyr Gly Pro Gly Ser Gly Gln Gly Pro Gly Gln Gln
                195                 200                 205

Gly Pro Gly Gln Gly Pro Tyr Gly Pro Gly Ala Ser Ala Ala Ala
                210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gly Pro Tyr Gly
                245                 250                 255

Pro Gly Ala Ser Ala Ala Ala Ala Ala Gly Gly Tyr Gly Pro Gly
                260                 265                 270

Tyr Gly Gln Gln Gly Pro Gly Gln Gln Gly Pro Gly Gln Gly Pro
                275                 280                 285
```

```
Tyr Gly Pro Gly Ala Ser Ala Ala Ser Ala Ala Gly Gly Tyr Gly
        290                 295                 300
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Gly Gly
                325                 330                 335
Tyr Gly Pro Gly Ser Gly Gln Gln Gly Pro Gly Gln Gln Gly Pro Gly
                340                 345                 350
Gln Gln Gly Pro Gly Gln Gln Gly Pro Gly Gln Gln Gly Pro Tyr Gly
        355                 360                 365
Pro Gly Ala Ser Ala Ala Ala Ala Ala Ala Gly Gly Tyr Gly Pro Gly
370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
                405                 410                 415
Gln Gln Gly Pro Gly Gln Gln Gly Pro Gly Gln Gln Gly Pro Gly Gly
                420                 425                 430
Gln Gly Ala Tyr Gly Pro Gly Ala Ser Ala Ala Ala Gly Ala Ala Gly
        435                 440                 445
Gly Tyr Gly Pro Gly Ser Gly Gln Gln Gly Pro Gly Gln Gln Gly Pro
450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
                485                 490                 495
Pro Gly Ala Ser Ala Ala Ala Ala Ala Ala Gly Gly Tyr Gly Pro Gly
                500                 505                 510
Ser Gly Gln Gln Gly Pro Gly Gln Gln Gly Pro Gly Gln Gln Gly Pro
        515                 520                 525
Gly Gly Gln Gly Pro Tyr Gly Pro Gly Ala Ala Ser Ala Ala Val Ser
        530                 535                 540
Val Ser Arg Ala Arg Ala Gly Ser Gly Gln Gln Gly Pro Gly Gln Gln
545                 550                 555                 560
Gly Pro Gly Gln Gln Gly Pro Gly Gln Gln Gly Pro Tyr Gly Pro Gly
                565                 570                 575
Ala Ser Ala Ala Ala Ala Ala Ala Gly Gly Tyr Gly Pro Gly Ser Gly
                580                 585                 590
Gln Gln Gly Pro Ser Gln Gln Gly Pro Gly Gln Gln Gly Pro Gly Gly
        595                 600                 605
Gln Gly Pro Tyr Gly Pro Gly Ala Ser Ala Ala Ala Ala Ala Ala Gly
        610                 615                 620
Gly Tyr Gly Pro Gly Ser Gly Gln Gln Gly Pro Gly Gly Gln Gly Pro
625                 630                 635                 640
Tyr Gly Pro Gly Ser Ser Ala Ala Ala Ala Ala Gly Gly Asn Gly
                645                 650                 655
Pro Gly Ser Gly Gln Gln Gly Ala Gly Gln Gln Gly Pro Gly Gln Gln
                660                 665                 670
Gly Pro Gly Ala Ser Ala Ala Ala Ala Ala Gly Gly Tyr Gly Pro
        675                 680                 685
Gly Ser Gly Gln Gln Gly Pro Gly Gln Gln Gly Pro Gly Gly Gln Gly
        690                 695                 700
```

-continued

```
Pro Tyr Gly Pro Gly Ala Ser Ala Ala Ala Ala Ala Gly Gly Tyr
705                 710                 715                 720

Gly Pro Gly Ser Gly Gln Gly Pro Gly Gln Gln Gly Pro Gly Gln
            725                 730                 735

Gly Pro Tyr Gly Pro Gly Ala Ser Ala Ala Ala Ala Ala Gly Gly
            740                 745                 750

Tyr Gly Pro Gly Ser Gly Gln Gln Gly Pro Gly Gln Gln Gly Pro Gly
            755                 760                 765

Gln Gln Gly Pro Gly Gly Gln Gly Pro Tyr Gly Pro Gly Ala Ser Ala
        770                 775                 780

Ala Ala Ala Ala Ala Gly Gly Tyr Gly Pro Gly Tyr Gly Gln Gln Gly
785                 790                 795                 800

Pro Gly Gln Gln Gly Pro Gly Gln Gly Pro Tyr Gly Pro Gly Ala
            805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gln Gly Pro Tyr Gly Pro
        835                 840                 845

Gly Ala Ser Ala Ala Ala Ala Ala Gly Gly Tyr Gly Pro Gly Ser
850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
            885                 890                 895

Ala Ala Ala Ala Gly Gly Tyr Gly Pro Gly Ser Gly Gln Gln Gly
900                 905                 910

Pro Gly Gln Gln Gly Pro Gly Gln Gln Gly Pro Gly Gln Gln Gly Pro
            915                 920                 925

Gly Gln Gln Gly Pro Gly Gln Gln Gly Pro Gly Gln Gln Gly Pro Gly
            930                 935                 940

Gln Gln Gly Pro Gly Gln Gln Gly Pro Gly Gly Gln Gly Ala Tyr Gly
945                 950                 955                 960

Pro Gly Ala Ser Ala Ala Ala Gly Ala Ala Gly Gly Tyr Gly Pro Gly
            965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln Gly Pro Gly Gln Gln Gly Pro Gly
        995                 1000                1005

Gln Gln Gly Pro Gly Gln Gln Gly Pro Tyr Gly Pro Gly Ala Ser
    1010                1015                1020

Ala Ala Ala Ala Ala Gly Gly Tyr Gly Pro Gly Ser Gly Gln
    1025                1030                1035

Gln Gly Pro Gly Gln Gln Gly Pro Gly Gln Gln Gly Pro Gly Gly
    1040                1045                1050

Gln Gly Pro Tyr Gly Pro Gly Ala Ala Ser Ala Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
```

-continued

```
                1115                1120                1125

Ser Asn Pro Gly Leu Ser Gly Cys Asp Val Leu Val Gln Ala Leu
        1130                1135                1140

Leu Glu Val Val Ser Ala Leu Val Ser Ile Leu
    1145                1150

<210> SEQ ID NO 3
<211> LENGTH: 660
<212> TYPE: PRT
<213> ORGANISM: Artificial
<220> FEATURE:
<223> OTHER INFORMATION: ADF3Kai

<400> SEQUENCE: 3

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala
        115                 120                 125

Ala Gly Gly Asn Gly Pro Gly Ser Gly Gln Gln Gly Ala Gly Gln Gln
        130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Ala Gly Gly
```

```
                    325                 330                 335

Tyr Gly Pro Gly Ser Gly Gln Gln Gly Pro Gly Gln Gln Pro Gly
                    340                 345                 350

Gln Gln Gly Pro Gly Gln Gln Gly Pro Gly Gln Gly Pro Tyr Gly
                    355                 360                 365

Pro Gly Ala Ser Ala Ala Ala Ala Ala Gly Gly Tyr Gly Pro Gly
                    370                 375                 380

Ser Gly Gln Gln Gly Pro Gly Gln Gln Gly Pro Gly Gln Gln Gly Pro
        385                 390                 395                 400

Gly Gln Gln Gly Pro Gly Gln Gln Gly Pro Gly Gln Gln Gly Pro Gly
                    405                 410                 415

Gln Gln Gly Pro Gly Gln Gln Gly Pro Gly Gln Gln Gly Pro Gly Gly
                    420                 425                 430

Gln Gly Ala Tyr Gly Pro Gly Ala Ser Ala Ala Gly Ala Ala Gly
                    435                 440                 445

Gly Tyr Gly Pro Gly Ser Gly Gln Gln Gly Pro Gly Gln Gln Gly Pro
                    450                 455                 460

Gly Gln Gln Gly Pro Gly Gln Gln Gly Pro Gly Gln Gln Gly Pro Gly
        465                 470                 475                 480

Gln Gln Gly Pro Gly Gln Gln Gly Pro Gly Gln Gln Gly Pro Tyr Gly
                    485                 490                 495

Pro Gly Ala Ser Ala Ala Ala Ala Ala Gly Gly Tyr Gly Pro Gly
                    500                 505                 510

Ser Gly Gln Gln Gly Pro Gly Gln Gln Gly Pro Gly Gln Gln Gly Pro
                    515                 520                 525

Gly Gly Gln Gly Pro Tyr Gly Pro Gly Ala Ala Ser Ala Ala Val Ser
                    530                 535                 540

Val Gly Gly Tyr Gly Pro Gln Ser Ser Val Pro Val Ala Ser Ala
        545                 550                 555                 560

Val Ala Ser Arg Leu Ser Ser Pro Ala Ala Ser Ser Arg Val Ser Ser
                    565                 570                 575

Ala Val Ser Ser Leu Val Ser Ser Gly Pro Thr Lys His Ala Ala Leu
                    580                 585                 590

Ser Asn Thr Ile Ser Ser Val Val Ser Gln Val Ser Ala Ser Asn Pro
                    595                 600                 605

Gly Leu Ser Gly Cys Asp Val Leu Val Gln Ala Leu Leu Glu Val Val
                    610                 615                 620

Ser Ala Leu Val Ser Ile Leu Gly Ser Ser Ile Gly Gln Ile Asn
        625                 630                 635                 640

Tyr Gly Ala Ser Ala Gln Tyr Thr Gln Met Val Gly Gln Ser Val Ala
                    645                 650                 655

Gln Ala Leu Ala
                    660

<210> SEQ ID NO 4
<211> LENGTH: 1183
<212> TYPE: PRT
<213> ORGANISM: Artificial
<220> FEATURE:
<223> OTHER INFORMATION: ADF3Kai-Large

<400> SEQUENCE: 4

Met His His His His His His His His His His Ser Ser Gly Ser Ser
1               5                   10                  15

Leu Glu Val Leu Phe Gln Gly Pro Ala Arg Ala Gly Ser Gly Gln Gln
```

```
                    20                  25                  30
Gly Pro Gly Gln Gln Gly Pro Gly Gln Gln Gly Pro Gly Gln Gln Gly
                35                  40                  45
Pro Tyr Gly Pro Gly Ala Ser Ala Ala Ala Ala Ala Gly Gly Tyr
            50                  55                  60
Gly Pro Gly Ser Gly Gln Gly Pro Ser Gln Gly Pro Gly Gln
65                  70                  75                  80
Gln Gly Pro Gly Gln Gly Pro Tyr Gly Pro Gly Ala Ser Ala Ala
                85                  90                  95
Ala Ala Ala Ala Gly Gly Tyr Gly Pro Gly Ser Gly Gln Gln Gly Pro
            100                 105                 110
Gly Gly Gln Gly Pro Tyr Gly Pro Gly Ser Ser Ala Ala Ala Ala
            115                 120                 125
Ala Gly Gly Asn Gly Pro Gly Ser Gly Gln Gln Gly Ala Gly Gln Gln
            130                 135                 140
Gly Pro Gly Gln Gln Gly Pro Gly Ala Ser Ala Ala Ala Ala Ala
145                 150                 155                 160
Gly Gly Tyr Gly Pro Gly Ser Gly Gln Gln Gly Pro Gly Gln Gln Gly
                165                 170                 175
Pro Gly Gly Gln Gly Pro Tyr Gly Pro Gly Ala Ser Ala Ala Ala Ala
            180                 185                 190
Ala Ala Gly Gly Tyr Gly Pro Gly Ser Gly Gln Gly Pro Gly Gln Gln
            195                 200                 205
Gly Pro Gly Gly Gln Gly Pro Tyr Gly Pro Gly Ala Ser Ala Ala Ala
            210                 215                 220
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gln Gln Gly Pro Tyr Gly
                245                 250                 255
Pro Gly Ala Ser Ala Ala Ala Ala Ala Gly Gly Tyr Gly Pro Gly
            260                 265                 270
Tyr Gly Gln Gln Gly Pro Gly Gln Gln Gly Pro Gly Gln Gln Gly Pro
            275                 280                 285
Tyr Gly Pro Gly Ala Ser Ala Ala Ser Ala Ala Ser Gly Gly Tyr Gly
            290                 295                 300
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Gly Gly
                325                 330                 335
Tyr Gly Pro Gly Ser Gly Gln Gln Gly Pro Gly Gln Gln Gly Pro Gly
            340                 345                 350
Gln Gln Gly Pro Gly Gln Gln Gly Pro Gly Gly Gln Gly Pro Tyr Gly
            355                 360                 365
Pro Gly Ala Ser Ala Ala Ala Ala Ala Gly Gly Tyr Gly Pro Gly
            370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
                405                 410                 415
Gln Gln Gly Pro Gly Gln Gln Gly Pro Gly Gln Gln Gly Pro Gly Gly
            420                 425                 430
Gln Gly Ala Tyr Gly Pro Gly Ala Ser Ala Ala Ala Gly Ala Ala Gly
            435                 440                 445
```

-continued

```
Gly Tyr Gly Pro Gly Ser Gly Gln Gln Gly Pro Gly Gln Gln Gly Pro
            450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
                485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
            515                 520                 525
Gly Gly Gln Gly Pro Tyr Gly Pro Gly Ala Ala Ser Ala Ala Val Ser
            530                 535                 540
Val Ser Arg Ala Arg Ala Gly Ser Gly Gln Gln Gly Pro Gly Gln Gln
545                 550                 555                 560
Gly Pro Gly Gln Gln Gly Pro Gly Gln Gln Gly Pro Tyr Gly Pro Gly
                565                 570                 575
Ala Ser Ala Ala Ala Ala Ala Gly Gly Tyr Gly Pro Gly Ser Gly
            580                 585                 590
Gln Gln Gly Pro Ser Gln Gln Gly Pro Gly Gln Gln Gly Pro Gly Gly
            595                 600                 605
Gln Gly Pro Tyr Gly Pro Gly Ala Ser Ala Ala Ala Ala Ala Gly
            610                 615                 620
Gly Tyr Gly Pro Gly Ser Gly Gln Gln Gly Pro Gly Gln Gln Gly Pro
625                 630                 635                 640
Tyr Gly Pro Gly Ser Ser Ala Ala Ala Ala Ala Gly Gly Asn Gly
            645                 650                 655
Pro Gly Ser Gly Gln Gln Gly Ala Gly Gln Gln Gly Pro Gly Gln Gln
            660                 665                 670
Gly Pro Gly Ala Ser Ala Ala Ala Ala Ala Gly Gly Tyr Gly Pro
            675                 680                 685
Gly Ser Gly Gln Gln Gly Pro Gly Gln Gln Gly Pro Gly Gly Gln Gly
            690                 695                 700
Pro Tyr Gly Pro Gly Ala Ser Ala Ala Ala Ala Ala Gly Gly Tyr
705                 710                 715                 720
Gly Pro Gly Ser Gly Gln Gly Pro Gly Gln Gln Gly Pro Gly Gly Gln
                725                 730                 735
Gly Pro Tyr Gly Pro Gly Ala Ser Ala Ala Ala Ala Ala Gly Gly
            740                 745                 750
Tyr Gly Pro Gly Ser Gly Gln Gln Gly Pro Gly Gln Gln Gly Pro Gly
            755                 760                 765
Gln Gln Gly Pro Gly Gly Gln Gly Pro Tyr Gly Pro Gly Ala Ser Ala
            770                 775                 780
Ala Ala Ala Ala Gly Gly Tyr Gly Pro Gly Tyr Gly Gln Gln Gly
785                 790                 795                 800
Pro Gly Gln Gln Gly Pro Gly Gly Gln Gly Pro Tyr Gly Pro Gly Ala
                805                 810                 815
Ser Ala Ala Ser Ala Ala Ser Gly Gly Tyr Gly Pro Gly Ser Gly Gln
            820                 825                 830
Gln Gly Pro Gly Gln Gln Gly Pro Gly Gly Gln Gly Pro Tyr Gly Pro
            835                 840                 845
Gly Ala Ser Ala Ala Ala Ala Ala Gly Gly Tyr Gly Pro Gly Ser
            850                 855                 860
```

```
Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
                885                 890                 895

Ala Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gln Gly Ala Tyr Gly
945                 950                 955                 960

Pro Gly Ala Ser Ala Ala Ala Gly Ala Ala Gly Gly Tyr Gly Pro Gly
                965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln Gly Pro Gly Gln Gln Gly Pro Gly
        995                 1000                1005

Gln Gln Gly Pro Gly Gln Gln Gly Pro Tyr Gly Pro Gly Ala Ser
    1010                1015                1020

Ala Ala Ala Ala Ala Gly Gly Tyr Gly Pro Gly Ser Gly Gln
    1025                1030                1035

Gln Gly Pro Gly Gln Gln Gly Pro Gly Gln Gln Gly Pro Gly Gly
    1040                1045                1050

Gln Gly Pro Tyr Gly Pro Gly Ala Ala Ser Ala Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu Gly Ser Ser Ser
    1145                1150                1155

Ile Gly Gln Ile Asn Tyr Gly Ala Ser Ala Gln Tyr Thr Gln Met
    1160                1165                1170

Val Gly Gln Ser Val Ala Gln Ala Leu Ala
    1175                1180

<210> SEQ ID NO 5
<211> LENGTH: 24
<212> TYPE: PRT
<213> ORGANISM: Artificial
<220> FEATURE:
<223> OTHER INFORMATION: His tag and start codon

<400> SEQUENCE: 5

Met His His His His His His His His His Ser Ser Gly Ser Ser
1               5                   10                  15

Leu Glu Val Leu Phe Gln Gly Pro
            20
```

```
<210> SEQ ID NO 6
<211> LENGTH: 1626
<212> TYPE: DNA
<213> ORGANISM: Artificial
<220> FEATURE:
<223> OTHER INFORMATION: ADF3Kai-NN

<400> SEQUENCE: 6
atgcatcacc atcatcatca tcaccaccac cattcctcgg gctcatcctt ggaagtgtta      60
tttcaaggac cagcacgagc cggttcggga caacaagggc ctggccagca gggcccaggt     120
caacaagggc caggacagca gggtccttat gggcccggcg caagcgcagc agctgcggcc     180
gctggtggct atggtcctgg ctccggtcaa cagggcccct cgcaacaagg tcccgggcag     240
caaggtcctg gtggccaggg tccctacggg ccggggcga gtgcggcagc agccgctgca     300
ggcggttatg gtccaggaag cggacagcaa ggtccggag gtcaaggtcc gtatggccca     360
ggctctagcg cggctgccgc tgccgcgggt ggcaacggac agggagcgg acaacagggc     420 gcgggacaac agggtccagg acagcaaggc caggggcgt cggcggctgc agcggcggcc     480
ggaggctatg acccggctc aggacaacag ggaccgggtc aacaaggacc cggtggccaa     540
ggcccctatg cccgggcgc cagcgcggcc gcagccgccg cgggcgggta cggccccggt     600
agcggccagg gaccaggtca gcaggggcca ggaggtcagg gcccatacgg tccgggcgca     660
tccgcggcgg cggcagcggc aggtggctac ggtcccggaa gcggccaaca ggggccaggg     720
caacaaggac caggacaaca aggtcctggg ggccaaggac cgtatggacc aggagcatca     780
gctgcagccg cggcagctgg cggttacggt ccaggctacg ccagcaggg tccgggtcag     840 cagggaccgg gaggccaggg gccttatggc cctggcgctt ccgcagccag tgccgcttct     900
ggaggatacg ggccgggaag cggtcagcaa ggccctggcc aacaaggacc tggaggccaa     960
gggccctacg gccaggagc ctcggcagcc gcagctgccg caggtgggta tgggccaggt    1020
agcgggcaac aagggccggg tcagcaagga ccggggcaac agggacctgg gcagcaagga    1080
cccgggggtc aaggcccgta cggacctggt gcgtctgcag ctgctgctgc ggctggtgga    1140
tatggtccgg gatcggggca gcagggtccc ggtcagcagg gcctggtca gcaagggcca    1200 ggccaacagg gacccggaca acaaggcccg ggtcaacagg gtcctggaca gcagggccgg    1260
ggccaacaag gccctgggca acaggtccg ggggacagg gggcctatgg gcctggcgca    1320
tctgccgccg ctggcgcagc cggtgggtac gggcctgggt caggtcaaca ggggcctggt    1380
caacaaggcc ccgggcaaca gggcccggc cagcaaggtc agggcagca gggcccggga    1440 cagcaagggc ctggacaaca ggggcccgga cagcaggac cttacgggcc cggtgcgagc    1500
gcagcggccg ccgccgcagg gggatatggc cccggatcgg gccagcaggg accaggccag    1560
caaggacctg gccaacaggg cccggggggt caggggccgt atggtcccgg cgctgcaagt    1620
gctgca                                                              1626
```